United States Patent
Morreale et al.

(10) Patent No.: US 11,859,759 B2
(45) Date of Patent: Jan. 2, 2024

(54) SUPPORT STAND FOR MAGNETIC RESONANCE IMAGING SCANNER

(71) Applicant: Synaptive Medical Inc., Toronto (CA)

(72) Inventors: Mark Tullio Morreale, Toronto (CA); Alex Gyles Panther, Toronto (CA); Geneviève Rodrigue, Toronto (CA)

(73) Assignee: Synaptive Medical Inc., Toronto (CA)

( * ) Notice: Subject to any disclaimer, the term of this patent is extended or adjusted under 35 U.S.C. 154(b) by 1520 days.

(21) Appl. No.: 16/122,152

(22) Filed: Sep. 5, 2018

(65) Prior Publication Data
US 2020/0072408 A1  Mar. 5, 2020

(51) Int. Cl.
*F16M 11/20* (2006.01)
*G01R 33/28* (2006.01)
*A61B 5/055* (2006.01)

(52) U.S. Cl.
CPC ........... *F16M 11/20* (2013.01); *A61B 5/055* (2013.01); *G01R 33/28* (2013.01)

(58) Field of Classification Search
None
See application file for complete search history.

(56) References Cited

U.S. PATENT DOCUMENTS

| | | | | |
|---|---|---|---|---|
| 5,016,638 A * | 5/1991 | Hsieh | ................... | G01R 33/421 324/309 |
| 5,793,210 A | 8/1998 | Pla et al. | | |
| 6,375,147 B1 * | 4/2002 | Radziun | ............ | G01R 33/3854 248/550 |
| 6,556,012 B2 * | 4/2003 | Yamashita | ......... | G01R 33/3854 324/309 |
| 6,703,836 B2 | 3/2004 | Ladebeck et al. | | |
| 6,774,633 B2 * | 8/2004 | Wang | ................. | G01R 33/3806 324/318 |
| 6,894,498 B2 | 5/2005 | Edelstein | | |

(Continued)

FOREIGN PATENT DOCUMENTS

WO    WO-2013042589 A1 *  3/2013 ............. A61B 5/055

OTHER PUBLICATIONS

Bilz Vibration Technology: "Paramed MRI", retrieved from http://bilz-usa.com/wp-content/uploads/2014/02/Paramed-MRI.pdf on Apr. 3, 2018.

(Continued)

*Primary Examiner* — Rodney E Fuller
(74) *Attorney, Agent, or Firm* — Rowand LLP

(57) ABSTRACT

A support stand for supporting a magnetic resonance imaging (MRI) scanner while in operation. A MRI scanner includes a cylindrical housing having a lateral surface extending parallel to a horizontal patient bore to encapsulate a main cylindrical magnet. The cylindrical housing defines a longitudinal footprint dimension and a lateral footprint dimension. The support stand includes a base and a plurality of pillars extending upright from the base. Each respective pillar includes a first end mounted to the base and an opposing second end. The support stand also includes a vibration isolator mounted at the second end of the respective pillars to support the lateral surface of the cylindrical housing. The respective vibration isolators minimize transmission of environment borne vibrations to the MRI scanner or minimize transmission of MRI scanner generated vibrations to the environment.

20 Claims, 8 Drawing Sheets

(56) References Cited

U.S. PATENT DOCUMENTS

| | | | |
|---|---|---|---|
| 6,954,068 B1* | 10/2005 | Takamori | G01R 33/3854 324/318 |
| 8,083,076 B2 | 12/2011 | Hobbs et al. | |
| 2001/0022515 A1* | 9/2001 | Yamashita | G01R 33/3854 324/300 |
| 2002/0118015 A1* | 8/2002 | Ham | G01R 33/3854 324/318 |
| 2006/0006866 A1* | 1/2006 | Roozen | G01R 33/3854 324/318 |
| 2018/0059196 A1 | 3/2018 | Takamori et al. | |
| 2019/0146046 A1* | 5/2019 | Kralick | G01R 33/3802 248/205.1 |

OTHER PUBLICATIONS

Search Report issued by Intellectual Property Office of the United Kingdom in relation to corresponding GB Application No. GB1913088.9 dated Mar. 27, 2020, 3 pgs.

\* cited by examiner

SUPPORT STAND FOR MAGNETIC RESONANCE IMAGING SCANNER

FIELD

The present application relates to medical diagnostic systems and, in particular, to support stands for magnetic resonance imaging scanners.

BACKGROUND

Magnetic resonance imaging (MRI) scanners generate strong magnetic fields, electric field gradients, and radio frequency (RF) pulses for generating images of organs of the body. A patient or a portion of the patient is placed within a patient bore of the MRI scanner during imaging operations. The MRI scanner includes a main magnet for producing a static magnetic field within the patient bore, thereby causing protons of the organ under observation to align with the direction of the static magnetic field. The MRI scanner includes an RF coil for generating magnetic pulses for momentarily exciting protons in the static magnetic field, thereby causing momentary rotation of the respective protons away from the direction of the static magnetic field and back to the direction of the static magnetic field. As the respective protons realign with the static magnetic field, the respective protons release energy known as relaxation. The MRI scanner also includes a gradient coil having a switching frequency that produces a magnetic field with a linear gradient. The linear gradient isolates target protons of portions of the organ under observation to achieve resonance to produce an image.

Existing MRI scanners are bulky and heavy and often require specialized packaging for transportation. The specialized packaging is often discarded after MRI scanner installation. Further, because of the bulky size and mass of MRI scanners, medical facilities often require modification to entranceways to accommodate installation of MRI scanners in medical facilities and modification to floors to include additional structure and padding for supporting the weight of MRI scanners.

During operation, MRI scanners generate an appreciable amount of vibration and audible acoustic noise (e.g., knocking sounds) due to rapid and frequent changes in magnetic field orientation. The generated vibrations are transmitted to the environment in which the MRI scanner is installed. Further, environmentally generated vibrations detected at the MRI scanner can impact image capture performance of the MRI scanner. For example, closing doors or elevator movement can generate vibrations that can be propagated to the MRI scanner, thereby reducing image resolution or increasing the chance of imaging error at the MRI scanner. Accordingly, it would be desirable to provide improved support stands for isolating both MRI scanner generated and environmentally generated vibrations and for supporting MRI scanners during transport, installation in a medical facility, and operation.

BRIEF DESCRIPTION OF THE DRAWINGS

Reference will now be made, by way of example, to the accompanying drawings which show example embodiments of the present application, and in which.

Similar reference numerals may have been used in different figures to denote similar components.

DESCRIPTION OF EXAMPLE EMBODIMENTS

Figure 1:
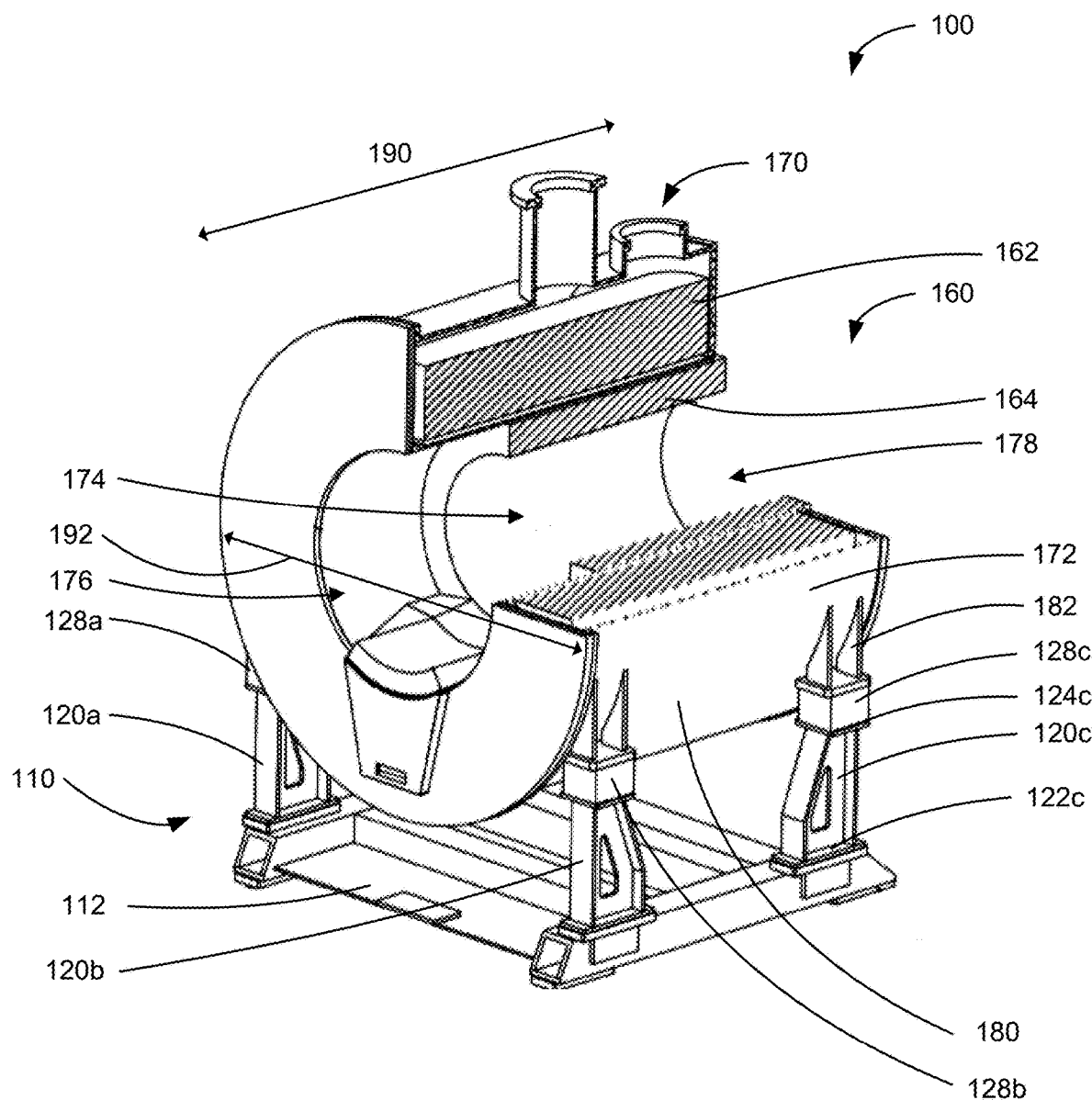
FIG. 1 illustrates a perspective, partial cutaway view of a MRI system, in accordance with an example of the present application.

Various examples and aspects of the present application will be described with reference to the details discussed herein. The following description and drawings are illustrative of the present application and are not to be construed as limiting the present application. Numerous details are described to provide a thorough understanding of various embodiments. However, in certain instances, well-known or conventional details are not described in order to provide a concise discussion of the embodiments of the present application.

In one aspect, the present application describes a support stand for supporting a magnetic resonance imaging (MRI) scanner while in operation, the MRI scanner including a cylindrical housing having a lateral surface extending parallel to a horizontal bore from a first bore end to a second bore end to encapsulate a main cylindrical magnet, the cylindrical housing defining a longitudinal footprint dimension and a lateral footprint dimension. The support stand includes: a base for positioning the support stand on a floor; a plurality of pillars extending upright from the base, each respective pillar having a first end mounted to the base and an opposing second end; and a vibration isolator mounted at the second end of respective pillars to support the lateral surface of the cylindrical housing, wherein a respective pillar in a pair of pillars is laterally separated from another pillar of that pair on an opposing lateral side of the horizontal bore by a lateral separation distance no greater than the lateral footprint dimension, and wherein a respective pillar in the plurality of pillars is longitudinally separated from another pillar in the plurality of pillars by a longitudinal separation distance no greater than the longitudinal footprint dimension.

In another aspect, the present application describes a magnetic resonance imaging (MRI) system including: a MRI scanner having a main cylindrical magnet with a horizontal bore extending parallel to a floor and extending from a first bore end to a second bore end; and a cylindrical housing encapsulating the main cylindrical magnet, the cylindrical housing having a lateral surface extending parallel to the horizontal bore from the first bore end to the second bore end, wherein the cylindrical housing defines a longitudinal footprint dimension and a lateral footprint dimension; and a support stand for supporting the MRI scanner while in operation, the support stand including: a base for positioning the support stand on the floor; a plurality of pillars extending upright from the base, each respective pillar having a first end mounted to the base and an opposing second end; and a vibration isolator mounted at the second end of respective pillars to support the lateral surface of the cylindrical housing, wherein a respective pillar in a pair of pillars is laterally separated from another pillar of that pair on an opposing lateral side of the horizontal bore by a lateral separation distance no greater than the lateral footprint dimension, and wherein a respective pillar in the plurality of pillars is longitudinally separated from another pillar in the plurality of pillars by a longitudinal separation distance no greater than the lateral footprint dimension.

Other aspects and features of the present application will be understood by those of ordinary skill in the art from a review of the following description of examples in conjunction with the accompanying figures.

In the present application, the terms "comprises" and "comprising" are intended to be inclusive and open ended, and not exclusive. Specifically, when used in the specification and claims, the terms "comprises" and "comprising" and variations thereof mean the specified features, steps, or components are included. These terms are not to be interpreted to exclude the presence of other features, steps, or components.

In the present application, the term "exemplary" means "serving as an example, instance, or illustration", and should not be construed as preferred or advantageous over other configurations disclosed herein.

In the present application, the terms "about", "approximately", and "substantially" are meant to cover variations that may exist in the upper and lower limits of the ranges of values, such as variations in properties, parameters, and dimensions. In a non-limiting example, the terms "about", "approximately", and "substantially" may mean plus or minus 10 percent or less.

In the present application, the term "and/or" is intended to cover all possible combinations and sub-combinations of the listed elements, including any one of the listed elements alone, any sub-combination, or all of the elements, and without necessarily excluding additional elements.

In the present application, the phrase "at least one of . . . or . . . " is intended to cover any one or more of the listed elements, including any one of the listed elements alone, any sub-combination, or all of the elements, without necessarily excluding any additional elements, and without necessarily requiring all of the elements.

Existing MRI scanners are bulky and heavy and require specialized packaging for transportation, such as framed containers and other shock absorbing materials. The specialized packaging is often discarded after shipment. To install MRI scanners at medical facilities, medical facilities often require modification, such as enlarging entranceway height or width and providing additional structure and padding for supporting the weight of MRI scanners.

During operation, MRI scanners generate an appreciable amount of vibration and audible acoustic noise (e.g., knocking sounds) due to rapid and frequent changes in magnetic field orientation. The generated vibrations are transmitted to the environment in which the MRI scanner is installed. Further, environmentally generated vibrations detected at the MRI scanner can impact image capture performance of the MRI scanner. For example, environmentally generated vibrations from nearby closing doors or elevator movement can generate vibrations that can be propagated to the MRI scanner, thereby reducing image resolution or increasing the chance of imaging error.

It would be desirable to provide an improved support stand for use during both transport and MRI scanner operation. Further, it would be desirable for the improved support stand to isolate MRI scanners from environmentally generated vibrations and to isolate the environment from the MRI scanner generated vibrations. Such an improved support stand is now provided.

Reference is made to FIG. 1, which illustrates a perspective, partial cutaway view of a MRI system 100, in accordance with an example of the present application. The MRI system 100 includes a support stand 110 for supporting a MRI scanner 160.

FIG. 1 illustrates a partial cutaway view of selected components of the MRI scanner 160. The MRI scanner 160 includes a main magnet 162, a gradient coil 164, and a radio frequency (RF) coil (not explicitly identified in FIG. 1). The MRI scanner 160 illustrated in FIG. 1 may be known as a closed-bore MRI scanner. The MRI scanner 160 includes a housing 172 for encapsulating at least the main magnet 162, the gradient coil 164, and the RF coil. The housing 172 is generally cylindrical in shape and includes a lateral surface 180 extending parallel to a patient bore 174. The patient bore 174 is a horizontally-oriented bore. The lateral surface 180 and the patient bore 174 may extend from a first bore end 176 to a second bore end 178. During operation, the patient or a portion of the patient under observation may be placed within the patient bore 174.

While in operation, the main magnet 162 generates a static magnetic field within the patient bore 174, thereby causing protons of organs under observation to align with the direction of the static magnetic field. The gradient coil 164 generates a magnetic field with a switching frequency that produces a magnetic field with a linear gradient. The linear gradient isolates target protons to achieve resonance to produce a target image. The RF coil generates magnetic pulses for momentarily exciting protons in the static magnetic field, thereby causing momentary rotation of the respective protons away from the direction of the static magnetic field and back to the direction of the static magnetic field. In some examples, the MRI scanner 160 includes a cryostat 170. The cryostat 170 may include components for maintaining the MRI scanner 160 within a desired operating temperature range.

As described, the housing 172 encapsulates at least the main magnet 162, the gradient coil 164, and the RF coil. The housing 172 is generally cylindrical in shape and may correspond at least to the shape of the main magnet 162. In FIG. 1, the housing 172 defines a longitudinal footprint dimension 190 and a lateral footprint dimension 192. As will be illustrated and described in the description herein, when seen from a top view, the housing 172 may have a generally rectangular footprint defined by the longitudinal footprint dimension 190 and the lateral footprint dimension 192. The longitudinal footprint dimension 190 is substantially a length of the housing 172 that extends from the first bore end 176 to the second bore end 178. The lateral footprint dimension 192 is substantially a diameter of the housing 172. The MRI scanner 160 illustrated in FIG. 1 is commonly known as a closed-bore MRI scanner; however, other types of MRI scanners, such as open-bore MRI scanners, can be contemplated.

The MRI system 100 also includes the support stand 110 for supporting the MRI scanner 160. The support stand 110 includes a base 112 for positioning the MRI system 100 on a floor within a medical facility. That is, when the MRI scanner 160 is mounted atop the support stand 110, the MRI scanner 160 can be maneuvered to its desired location within a medical facility using a wheeled mechanism for lifting and moving the base 112.

The support stand 110 includes a plurality of pillars, identified individually as 120a, 120b, and 120c in FIG. 1. Each of the plurality of pillars extends upright from the base 112. Further, each of the plurality of pillars includes a first end mounted to the base 112 and an opposing second end. As an illustrative example, the third pillar 120c includes a first end 122c mounted to the base 112 and a second end 124c.

The support stand 110 also includes a vibration isolator mounted at the second end of respective pillars to support the lateral surface 180 of the cylindrical housing 172. The respective vibration isolators are identified individually as 128a, 128b, and 128c in FIG. 1. For example, the third pillar 120c includes the first end 122c mounted to the base 112 and the third vibration isolator 128c mounted at the second end 124c to support the lateral surface 180 of the housing 172.

In some examples, the respective vibration isolators can directly interface with the lateral surface 180 of the cylindrical housing 172. In some other examples, the respective vibration isolators 128 can interface with standoffs 182 protruding or extending from the lateral surface 180 of the housing 172. For example, in FIG. 1, the standoffs 182 are illustrated as protruding from the lateral surface 180 of the housing 172 in a direction towards the base 112. There may be one or more standoffs 182 extending from the lateral surface 180 of the housing 172, where each respective standoff 182 is mounted to a respective vibration isolator. It can be appreciated that, in some examples, the standoffs 182 may not be needed.

Figure 2:
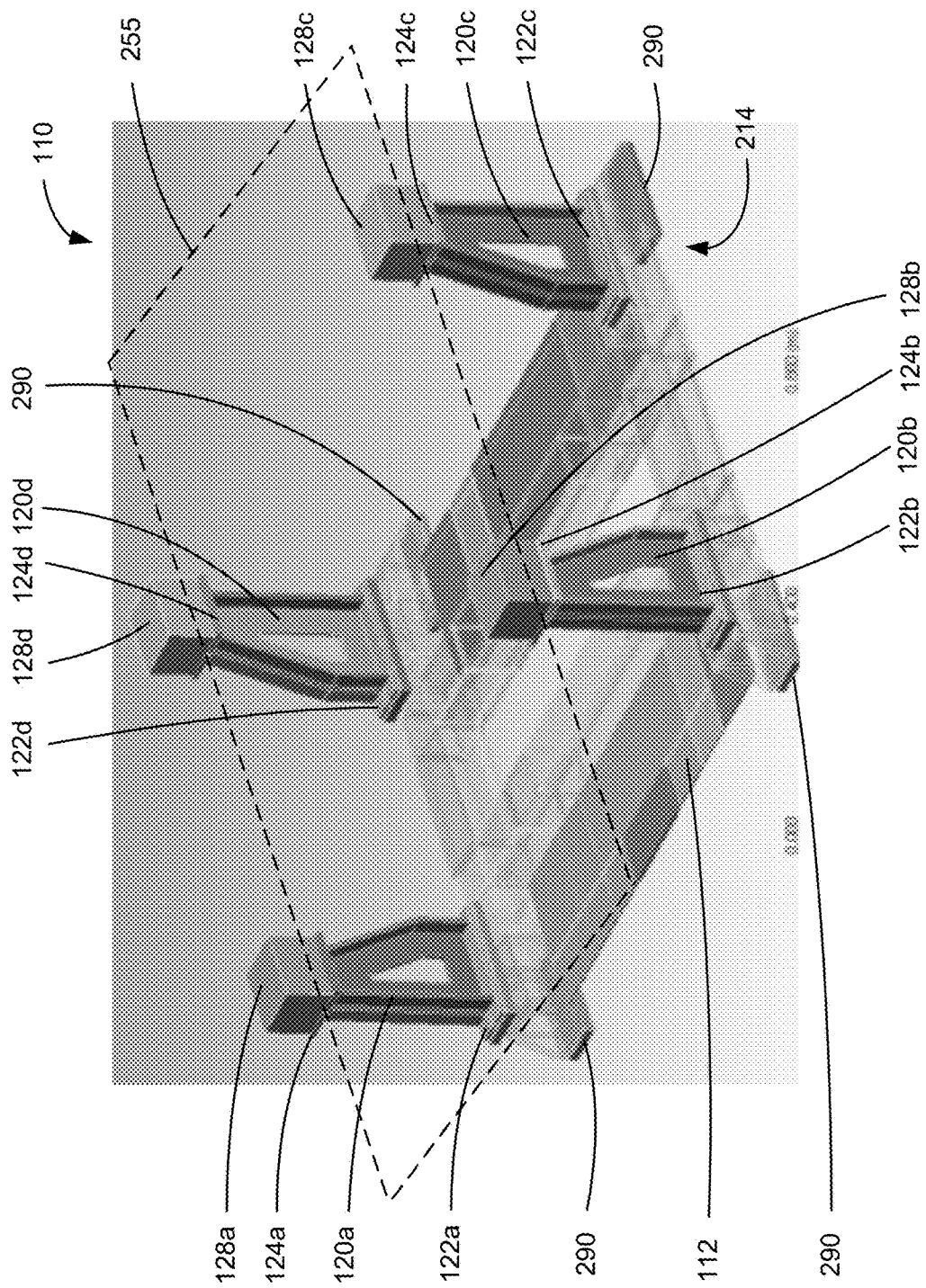
FIG. 2 illustrates a perspective view of the support stand of FIG. 1.

Reference is now made to FIG. 2, which illustrates a perspective view of the support stand 110 of FIG. 1. The support stand 110 includes the base 112 for positioning the support stand 110 on a floor of a medical facility. The medical facility can be a hospital environment, a private medical clinic, or any other facility requiring a MRI scanner. The base 112 can be generally rectangular and/or planar in shape; however, any other shape, such as oval, circular, etc. can be contemplated. In some examples, the base 112 can be welded or cast from non-magnetic and/or non-ferrous and/or non-magnetic material, such as aluminum, and is a combination of beams and planar support structures, as illustrated in FIG. 2. In some examples, the base may be constructed of substantially non-ferrous material including at least one of aluminum, SAE 316 stainless steel, fiberglass, plastic, brass, or epoxy. In some examples, the plastic, brass, or epoxy used for constructing the base is reinforced.

In FIG. 2, the base 112 is generally rectangular in shape and can include a number of mounting surfaces for mounting each of the plurality of pillars. The plurality of pillars include a first pillar 120a, a second pillar 120b, a third pillar 120c, and a fourth pillar 120d. The plurality of pillars extend upright from the base 112. In some examples, the plurality of pillars may be constructed of substantially non-ferrous and/or non-magnetic material, including at least one of aluminum, SAE 316 stainless steel or fiberglass.

Each respective pillar has a first end and a second end. For example, the first pillar 120a includes a first end 122a and a second end 124a. Similarly, the second pillar 120b includes a first end 122b and a second end 124b, the third pillar 120c includes a first end 122c and a second end 124c, and the fourth pillar 120d includes a first end 122d and a second end 124d.

The support stand 110 illustrated in FIG. 2 includes four pillars mounted substantially proximal to a corner of the substantially rectangular base to collectively form an equiangular quadrilateral perimeter. However, any number of pillars can be contemplated. For instance, the support stand 110 can include six pillars where pillars may be mounted substantially proximal to respective lateral edges of the base 112. In some other examples, the respective pillars may be mounted to the base at respective positions that may be inward from the respective lateral edges of the base 112.

During operation, MRI scanners generate appreciable amounts of vibrations that may be detected in the vicinity of the medical facility environment. MRI scanner generated vibrations can be unpleasant in the immediate surroundings and can be in the form of wall or floor vibrations akin to the effects of a minor earthquake. Further, MRI scanners can detect vibrations originating from the medical facility environment. Externally generated vibrations in the medical facility can originate from slamming doors or elevator movement, among other sources within the medical facility. Further, externally generated vibrations can originate from sources outside the medical facility, such as vehicles in a parking garage adjoining the medical facility, underground transit vehicles beneath the medical facility, etc. Externally generated vibrations detected at MRI scanners can impact the ability of the MRI scanner to accurately capture/generate images of a patient. It is desirable to provide an improved support stand to minimize the effect of: (a) MRI scanner generated vibrations on the immediate environment; and (b) externally generated vibrations on the operation of the MRI scanner. The support stand 110 is the primary mechanical medium between the MRI scanner 160 and the surrounding environment (e.g., room floor). Thus, it may be desirable to dampen vibrations at the interface between the support stand 110 and the MRI scanner.

The support stand 110 includes a vibration isolator mounted at the second end of respective pillars to support the lateral surface of a housing of an MRI scanner. For example, the support stand 110 includes a first vibration isolator 128a mounted at the second end 124a of the first pillar 120a. Similarly, a second vibration isolator 128b is mounted at the second end 124b of the second pillar 120b, a third vibration isolator 128c is mounted at the second end 124c of the third pillar 120c, and a fourth vibration isolator 128d is mounted at the second end 124d of the fourth pillar 120d.

In some examples, the respective vibration isolators include elastomeric material for minimizing transmission of floor-borne vibration to the MRI scanner 160 and for minimizing transmission of MRI scanner 160 generated vibration to the floor and the immediate environment. In some examples, the respective vibration isolators are a hollow elastomeric capsule for encapsulating a gas substance, such as air.

In some examples, the respective vibration isolators are air bladders that are adjustably inflatable with a pneumatic air supply source (not illustrated). For instance, the air bladders may include a valve coupled to a pneumatic air supply source via a hose or other conduit, and the pneumatic air supply source can include an air pressure sensor coupled to the respective air bladders and may be configured to detect the volume of air within the air bladders. In response to determining that the volume of air within the air bladders is less than a predetermined threshold, the pneumatic air supply can pump air to the air bladders. The vibration isolators can have a metallic exterior construction with a rubber air bladder contained therein.

To optimize vibration dampening and/or stabilizing effect of the support stand 110 for supporting an MRI scanner, the support stand 110 can be designed in concert with the MRI scanner 160 (FIG. 1). That is, the support stand 110 can be designed with the physical characteristics of the MRI scanner 160 in mind. To maximize the vibration dampening effect or the stabilizing effect of the support stand 110 on the MRI scanner 160, it may be desirable to minimize the distance between a center of gravity of the MRI scanner 160 and the respective vibration isolators. The center of gravity of the MRI scanner 160 is a unique point where the weighted relative position of distributed mass sum to zero. That is, the center of gravity is a point representing a mean position of the MRI scanner 160 as a whole such that when a force is applied to the center of gravity, the MRI scanner 160 may move in the direction of the applied force without rotating.

To minimize the distance between the center of gravity of the MRI scanner 160 and the respective vibration isolators, an isolation plane 255 is configured to intersect the center of gravity of the MRI scanner 160. The isolation plane 255 is a reference plane that intersects the respective second ends of the pillars or respective vibration isolators of the support stand 110. For example, the first vibration isolator 128a, the second vibration isolator 128b, the third vibration isolator 128c, and the fourth vibration isolator 128d may be in the isolation plane 255 and the isolation plane 255 is positioned upwards from the base 112. When each of the respective pillars (e.g., first pillar 120a, second pillar 120b, third pillar 120c, and fourth pillar 120d) are substantially the same length (e.g., distance from respective first ends to respective second ends), the isolation plane 255 is parallel to the base 112. Thus, to minimize the distance between the center of gravity of the MRI scanner 160 and the respective vibration isolators, the pillar lengths may be sized such that the isolation plane 255 is as near to the center of gravity of the MRI scanner 160 as possible. In some examples, the pillar lengths may be sized such that the isolation plane 255 intersects the center of gravity of the MRI scanner 160.

In some examples, each of the first vibration isolator 128a, the second vibration isolator 128b, the third vibration isolator 128c, or the fourth vibration isolator 128d can be individually sized or selected to include characteristics different than another of the vibration isolators. For example, the first vibration isolator 128a and the second vibration isolator 128b can be larger in size or can attenuate a different resonant frequency as compared to the third vibration isolator 128c and the fourth vibration isolator 128d. That is, if the main magnet has a greater weight at a longitudinal end nearest to the first vibration isolator 128a and the second vibration isolator 128b, the first vibration isolator 128a and the second vibration isolator 128b can be selected to be greater in size as compared to the third vibration isolator 128c and the fourth vibration isolator 128d.

In some examples, the vibration isolators are hollow capsules, metallic cylinders, or closed vessels for encapsulating air and the inflation pressure within respective vibration isolators can be selected based on a target resonant or natural frequency. It can be appreciated that when natural frequencies of non-linear vibration isolators approach substantially the same value, dynamic coupling among the vibration isolators can increase. When each respective vibration isolator is configured with a different inflation pressure thereby targeting a different natural vibration frequency, the collection of vibration isolators can provide greater vibration dampening than if the plurality of vibration isolators were configured with substantially the same inflation pressure. When each respective vibration isolator is configured with a slightly different target inflation pressure thereby targeting a different natural vibration frequency, there may be reduced dynamic coupling among the vibration isolators for providing greater vibration dampening than if the plurality of vibration isolators were configured with substantially the same inflation pressure.

It can be appreciated that a full body MRI scanner can include a main magnet having a larger diameter and corresponding center of gravity that may be higher from the medical facility floor than a smaller main magnet for a compact MRI scanner (e.g., MRI scanner for legs or arms). Thus, in some examples, the length of respective pillars on a large support stand for a full body MRI scanner may be greater than the length of respective pillars on a medium support stand for a compact MRI scanner having a center of gravity that may be nearer to the medical facility floor.

As illustrated, the respective pillars are mounted to and extend upright from the base 112 to support an associated MRI scanner. Thus, the respective second ends and respective vibration isolators mounted thereon support the MRI scanner from a position upwards from the medical facility floor and can cradle the MRI scanner housing. Further, in some examples, the vibration isolators mounted at the respective second ends can be fixed to the lateral surface 180 of the housing 172 such that the support stand 110 supports the MRI scanner during both transportation and operation.

The MRI scanner generated vibrations can be characterized by one or more resonant frequencies or harmonic vibration and thereby cause violent motion. In some examples, the support stand 110 can further include one or more tuned mass dampers coupled to at least one of the base 112 or one or more pillars for reducing harmonic vibration.

During transportation, it can be desirable to reduce the overall height of the MRI scanner that is supported by the support stand 110. In examples where the vibration isolators can be adjustably inflatable with a pneumatic air supply, the MRI scanner that is mounted to the respective pillars may be lowered in height relative to the base 112 during transport and may be raised in height relative to the base 112 during MRI scanner operation.

In some scenarios, the support stand 110 additionally includes one or more pads 290 affixed to a bottom base surface 214. For example, the one or more pads 290 may be rubber pads for attenuating vibrations greater than 60 Hz; however, any other types of pads may be used. In FIG. 2, the one or more pads 290 are positioned at peripheral corners of the base 112; however, the one or more pads 290 may be positioned across a plurality of positions on the bottom base surface 214.

In FIG. 2, a respective pillar in a pair of pillars is laterally separated from another pillar of that pair on an opposing lateral side of the horizontally-oriented patient bore 174 (FIG. 1) by a lateral separation distance no greater than the lateral footprint dimension 192 (FIG. 1). The lateral footprint dimension 192 can be a diameter of the housing 172 (FIG. 1) and, thus, the respective pillars of the support stand 110 are within the footprint of the MRI scanner 160.

For example, the first pillar 120a and the second pillar 120b may form a pair of pillars. The first pillar 120a is laterally separated from the second pillar 120b on an opposing lateral side of the horizontally-oriented patient bore 174. Similarly, the third pillar 120c and the fourth pillar 120d may form another pair of pillars, and the third pillar 120c is laterally separated from the fourth pillar 120d on an opposing lateral side of the horizontally-oriented patient bore 174.

Further, in FIG. 2, a respective pillar in the plurality of pillars is longitudinally separated from another pillar in the plurality of pillars by a longitudinal separation distance no greater than the longitudinal footprint dimension 190 (FIG.

1). The longitudinal footprint dimension 190 can be a length of the housing 172 (FIG. 1) and, thus, the respective pillars of the support stand 110 are within the footprint of the MRI scanner 160.

For example, the support stand 110 can be configured such that the first pillar 120a is longitudinally separated from the fourth pillar 120d by a longitudinal separation distance that is no greater than the longitudinal footprint dimension 190 (FIG. 1). Similarly, the first pillar 120a may be longitudinally separated from the second pillar 120b by a longitudinal separation distance that is no greater than the longitudinal footprint dimension 190 because the first pillar 120a and the second pillar 120b can have a longitudinal separation distance of substantially zero. Thus, the support stand 110 includes respective pillars mounted to the base 112 at positions that are within a footprint of the MRI scanner 160 (FIG. 1).

Figure 3A:
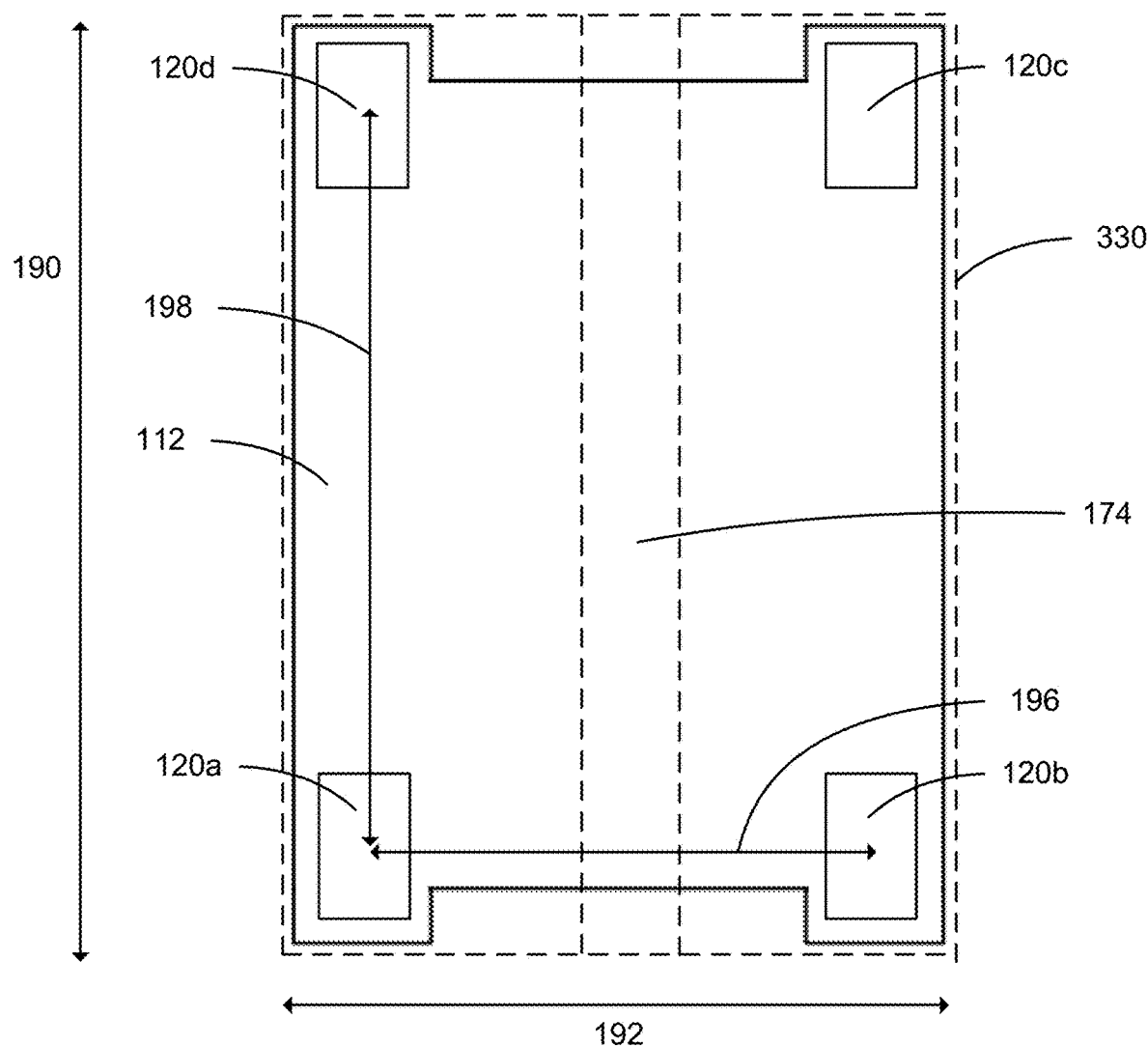
FIG. 3A illustrates a top view of a MRI scanner footprint overlaid on the support stand of FIG. 2.

To illustrate, reference is now made to FIG. 3A, which illustrates a top view of a MRI scanner footprint 330 overlaid on the support stand 110 of FIGS. 1 and 2, in accordance with an example of the present example. The MRI scanner footprint 330 is substantially rectangular and is similar in size to the base 112 of the support stand 110. However, in some other examples, the MRI scanner footprint 330 may be larger in size than the perimeter of the base 112.

As described, the MRI scanner footprint 330 is substantially rectangular and includes a longitudinal footprint dimension 190 and a lateral footprint dimension 192. FIG. 3A also illustrates the orientation of the patient bore 174 (FIG. 1) in hatched lines. In an example, the position at which the respective pillars, such as the first pillar 120a, the second pillar 120b, the third pillar 120c, and the fourth pillar 120d, are mounted to the base 112 is illustrated in FIG. 3A.

The first pillar 120a and the second pillar 120b may be identified as a pair of pillars and the first pillar 120a is laterally separated from the second pillar 120b on an opposing lateral side of the horizontally-oriented patient bore 174 by a lateral separation distance 196 that is no greater than the lateral footprint dimension 192. Similarly, the third pillar 120c is laterally separated from the fourth pillar 120d on an opposing lateral side of the horizontally-oriented patient bore 174 by a lateral separation distance that is no greater than the lateral footprint dimension 192.

In FIG. 3A, the first pillar 120a is longitudinally separated from the fourth pillar 120d by a longitudinal separation distance 198 that is no greater than the longitudinal footprint dimension 190. Thus, it can be appreciated that the support stand 110, including the respective pillars and the base 112, can have a support stand footprint area that is less than and within a MRI scanner footprint defined by the longitudinal footprint dimension 190 and the lateral footprint dimension 192. In the described configuration, the support stand 110 does not increase required floor area of the overall MRI system 100 (FIG. 1). It can be appreciated that although the MRI scanner footprint and the support stand footprint are illustrated to have a substantially rectangular perimeter, in some examples, the MRI scanner footprint can be any other shape and the support stand footprint can be any other shape that may be less than the total area of the MRI scanner footprint and within the MRI scanner footprint perimeter.

As MRI scanners are conventionally bulky in size and mass, transporting MRI scanners from production warehouses to medical facilities can be challenging. Because MRI scanners are conventionally placed on padded and/or support reinforced floors (e.g., concrete slabs), specialized equipment, such as cranes or hoists are often used for lifting MRI scanners and placing the MRI scanners into position within medical facilities. Thus, it may be desirable to provide support stands that may be used for supporting MRI scanners both during transport and operation.

Figure 3B:
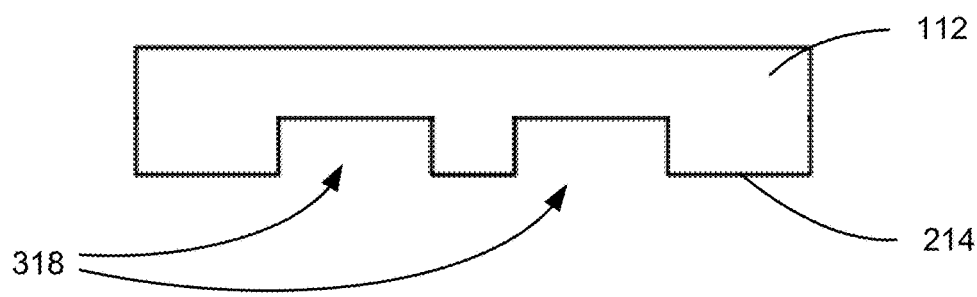
FIG. 3B illustrates a side elevation view of the base of the support stand of FIG. 3A.

Reference is now made to FIG. 3B, which illustrates a side elevation view of the base 112 of the support stand illustrated in FIG. 3A. Because the support stand can be fixed to the MRI scanner or the housing 172 of the MRI scanner, it may be desirable to adapt the support stand 110 to be lifted and maneuvered using a wheeled apparatus. The base 112 illustrated in FIG. 3B may be adapted to include features of a shipping pallet or skid. For example, the base 112 may include one or more base channels 318 in a bottom base surface 214 of the base 112. That is, the base channels 318 can be configured to receive a fork of a pallet jack operable to raise the support stand 110 (FIG. 1) and the MRI scanner 160 (FIG. 1) and move the MRI system 100 (FIG. 1) from one location to another location. In some examples, the pallet jack may be a conventional 27" wide pallet jack commonly found in warehouses and loading docks. Thus, when the MRI scanner 160 is supported by the support stand 110, the MRI scanner 160 may be transported and positioned at a medical facility without the need for cranes or hoists for placing the MRI scanner 160 in position on a medical facility floor. Further, the respective vibration isolators (e.g., first vibration isolator 128a, second vibration isolator 128b, third vibration isolator 128c, fourth vibration isolator 128d in FIG. 2) assist to provide support and shock attenuation during transportation of the MRI scanner, thereby decreasing the risk of damaging MRI scanner components.

Figure 4:
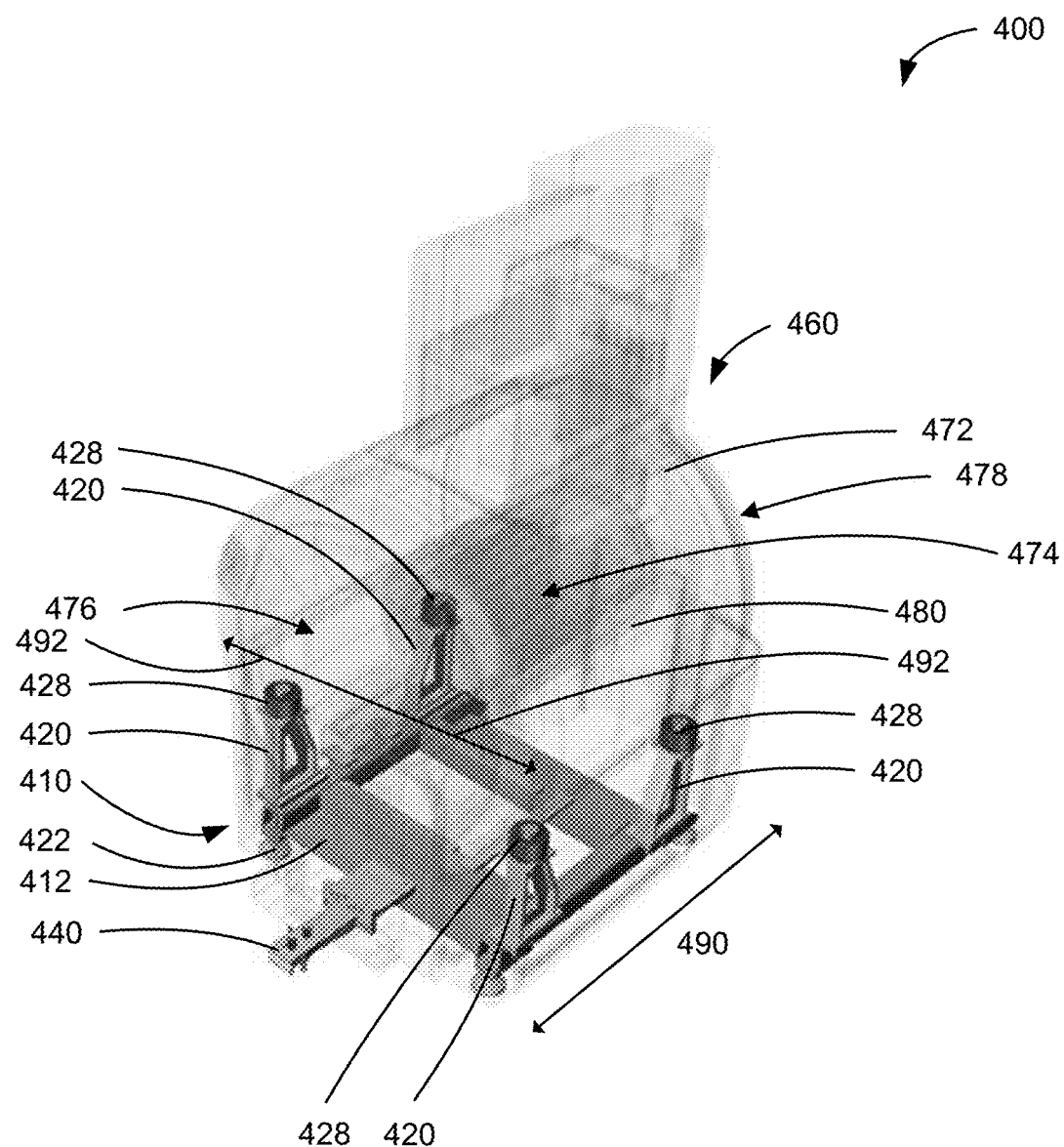
FIG. 4 illustrates a perspective view of a MRI system, in accordance with another example of the present application.

Reference is now made to FIG. 4, which illustrates a perspective view of a MRI system 400, in accordance with another example of the present application. The MRI system 400 includes a support stand 410 for supporting a MRI scanner 460.

The MRI scanner 460 includes a main cylindrical magnet having a horizontal bore 474 extending parallel to a floor and extending from a first bore end 476 to a second bore end 478. The MRI scanner 460 also includes a cylindrical housing 472 for encapsulating the main cylindrical magnet, among other components. Similar to the system of FIG. 1, the cylindrical housing 472 has a lateral surface 480 extending parallel to the horizontal bore 474 from the first bore end 476 to the second bore end 478. Best understood from a top view, the cylindrical housing 472 defines a longitudinal footprint dimension 490 and a lateral footprint dimension 492. It can be appreciated that the MRI scanner 460 includes other components, such as computer screens, computer systems, a cryostat, or other components.

The support stand 410 includes a base 412 for positioning the support stand 410 on the floor. In some examples, the base 412 may include one or more pads 422 affixed to a bottom base surface of the base 412 for attenuating vibrations originating from the environment floor or for attenuating vibrations originating from the MRI scanner 460 while in operation.

The support stand 410 includes a plurality of pillars 420 extending upright from the base 412. Each respective pillar 420 has a first end mounted to the base 412 and an opposing second end. The support stand 410 also includes a vibration isolator 428 mounted at the second end of respective pillars to support the lateral surface 480 of the cylindrical housing 472. Similar to the support stand of FIG. 2, a respective pillar in a pair of pillars is laterally separated from another pillar of that pair on an opposing lateral side of the horizontal bore by a lateral separation distance no greater than the lateral footprint dimension 492. Further, a respective pillar in the plurality of pillars 420 is longitudinally separated from another pillar in the plurality of pillars by a longitudinal separation distance no greater than the longitudinal footprint dimension 490.

In the example illustrated in FIG. 4, the cylindrical housing 472 may not include any standoffs (e.g., standoffs 182 of FIG. 1) and the lateral surface 480 may be supported by the vibration isolators 428 that are mounted to the respective pillars 420. In some examples, the second end of the respective pillars 420 includes a beveled surface to angle the respective vibration isolator 428 towards the lateral surface 480 to support the cylindrical housing. That is, the surface of the second end facing the lateral surface 480 may not be substantially parallel to the base, but is angled such that the surface of the second end is at an angle relative to the base.

The example support stand 410 illustrated in FIG. 4 further includes a docking module configured to secure a patient table to the support stand 410. For example, the docking module can include an attachment hook 440 proximal to the first bore end 476 of the cylindrical housing 472 for receiving a patient table. It can be appreciated that the attachment hook 440 can also be included proximal to the second bore end 478 of the cylindrical housing 472.

Figure 5:
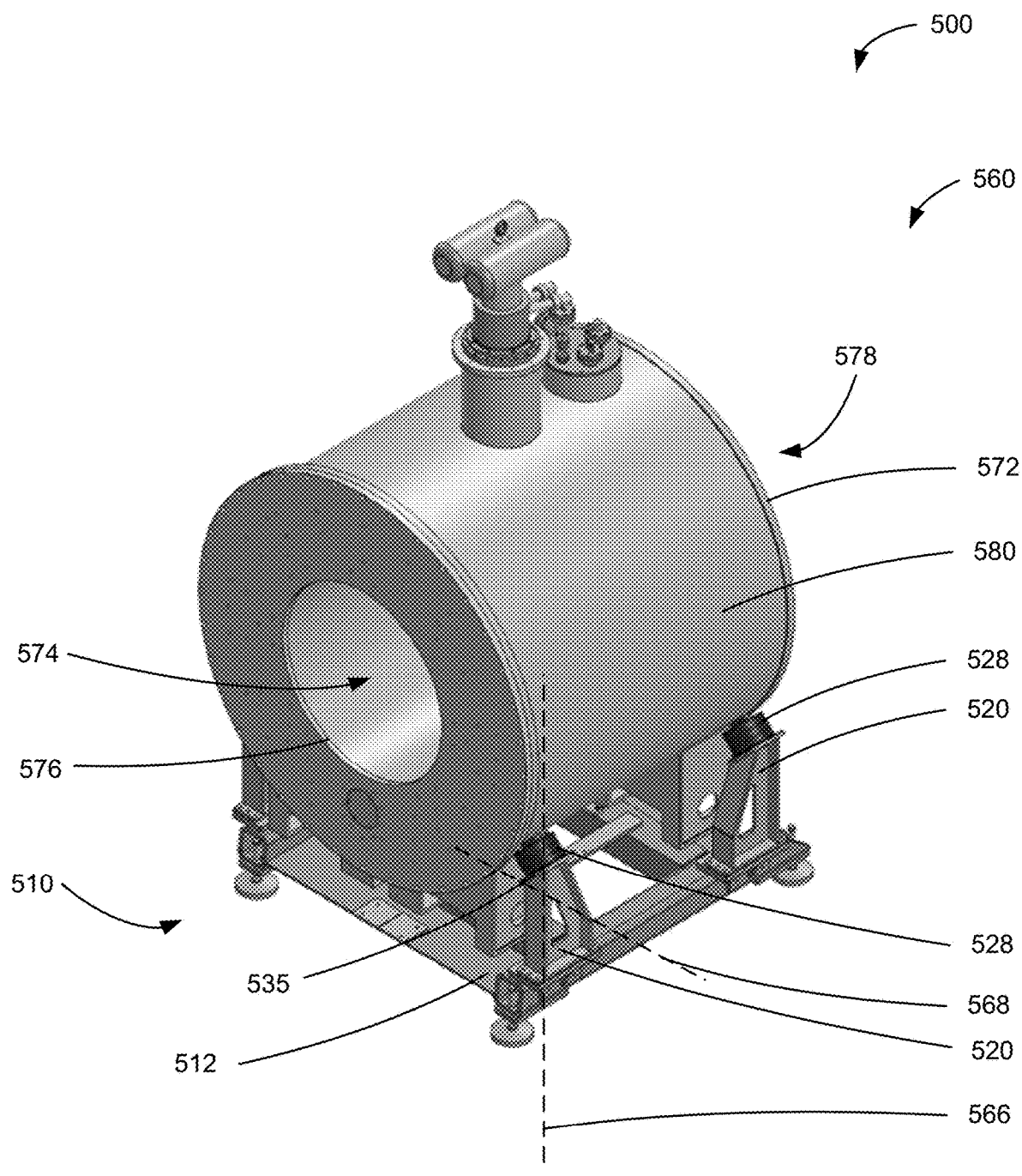
FIG. 5 illustrates a perspective view of a MRI system, in accordance with another example of the present application.

Reference is made to FIG. 5, which illustrates a perspective view of a MRI system 500, in accordance with another example of the present application. The MRI system 500 includes a support stand 510 for supporting a MRI scanner 560.

The MRI scanner 560 includes a main cylindrical magnet and includes a cylindrical housing 572 for encapsulating the main cylindrical magnet, among other components. Similar to the system of FIG. 4, the cylindrical housing 572 has a lateral surface 580 extending parallel to a horizontal bore 574 from a first bore end 576 to a second bore end 578. Similar to the system of FIG. 4, the cylindrical housing 572 defines a longitudinal footprint dimension and a lateral footprint dimension. It can be appreciated that the MRI scanner 560 includes other components, such as computer screens, computer systems, a cryostat, or other components.

The support stand 510 includes a base 512 for positioning the support stand 510 on the floor. In FIG. 5, the support stand 510 includes a plurality of pillars 520 extending upright from the base 512. Each respective pillar 520 has a first end mounted to the base 512 and an opposing second end. The support stand 510 also includes a vibration isolator 528 mounted at the second end of respective pillars to support the lateral surface 580 of the cylindrical housing 572. The cylindrical housing 572 may not include any standoffs and the lateral surface 580 may be supported by the vibration isolators 528 that are mounted to the respective pillars 520.

In the example illustrated in FIG. 5, the second end of the respective pillars 520 includes a beveled surface 535 to angle the respective vibration isolator 528 towards the lateral surface 580 to support the cylindrical housing 572. In FIG. 5, a first reference axis 566 (e.g., illustrated as a substantially vertical axis) and a second reference axis 568 (e.g., illustrated as a substantially horizontal axis, being substantially perpendicular to the first reference axis 566) is shown to highlight the beveled surface 535 at the second end of the respective pillars 520. That is, the surface of the second end of the respective pillars 520 that faces the lateral surface 580 may not be substantially parallel to the base 512, but is angled such that the surface of the second end is at an angle relative to the base 512.

In FIG. 5, the first reference axis 566 and the second reference axis 568 is illustrated for a single example pillar 520; however, each respective pillar 520 can similarly include a second end having an angled or beveled surface 535 relative to the base 512 for supporting the cylindrical housing 572.

In some examples described herein, an MRI scanner that is supported by an example support stand may be moved together as a unit. For example, as described herein with reference to FIG. 3B, a support stand having a MRI scanner supported thereon may be configured to receive forks of a pallet jack commonly found in warehouses and loading docks for transporting both the support stand and the MRI scanner from one location to another location. In some scenarios, it may be desirable, however, to transport the MRI scanner without the support stand or to raise the MRI scanner above the support stand. Examples features for facilitating the above will be described with reference to FIG. 6.

Figure 6:
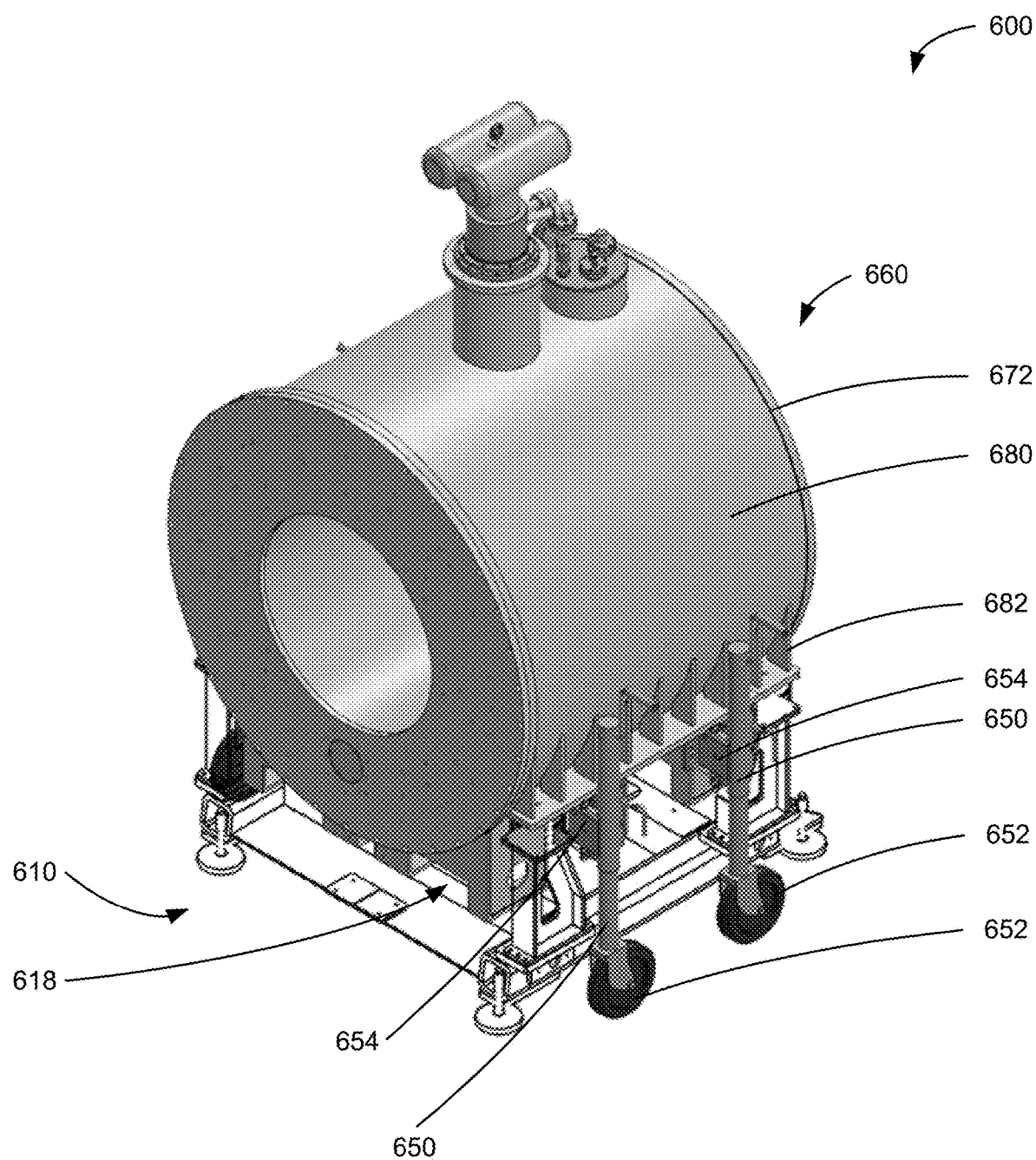
FIG. 6 illustrates a perspective view of a MRI system, in accordance with another example of the present application.

Reference is made to FIG. 6, which illustrates a perspective view of a MRI system 600, in accordance with another example of the present application. The MRI system 600 includes a support stand 610 for supporting an MRI scanner 660.

The MRI scanner 660 includes a main cylindrical magnet and includes a cylindrical housing 672 for encapsulating the main cylindrical magnet, among other components. Similar to the system of FIG. 5, the cylindrical housing 672 has a lateral surface 680 extending parallel to a horizontal bore from a first bore end to a second bore end. Similar to the system of FIG. 4, the cylindrical housing 672 defines a longitudinal footprint dimension and a lateral footprint dimension. It can be appreciated that the MRI scanner 660 includes other components, such as computer screens, computer systems, a cryostat, or other components.

As described, the cylindrical housing 672 has a lateral surface 680. The lateral surface 680 can include standoffs 682 protruding or extending from the lateral surface 680. The cylindrical housing 672 can include standoffs 682 on opposing lateral sides of the horizontal bore of the cylindrical housing 672 (note: in the perspective view of FIG. 6, standoffs 682 may be seen on one side of cylindrical housing 672).

In the example of FIG. 6, the standoffs 682 are illustrated as protruding from the lateral surface 680 of the housing 672 in a direction towards the base of the support stand 610. The standoffs can be mounted to one or more respective vibration isolators that are affixed to a second end of respective pillars.

In FIG. 6, the MRI system 600 includes one or more jacks 650. The one or more jacks 650 are arranged to support the cylindrical housing 672. For example, the standoffs 682 may be mounted on or resting on one or more jacks 650, as illustrated in FIG. 6. Each jack 650 may be an elongate structure having a mounting platform 654. The standoffs 682 can rest atop a surface of the mounting platform 654 of a jack 650 such that the MRI scanner 660 is supported by the standoffs 682. In some examples, the jack 650 can be an extendible elongate structure that can be adjusted to extend to the height of the standoffs 682 relative to the ground. In some examples, each jack 650 can include a wheel 652, such as a caster wheel, such that the MRI scanner 660 can be transported from one location to another location while being supported by one or more jacks 650.

In some examples, cylindrical housing 672 can include one or more housing base channels 618. The housing base channels 618 can be configured to receive a fork of a pallet jack operable to raise the cylindrical housing 672 of the MRI scanner 660 and to move the MRI scanner 660 from one location to another location.

In some scenarios, it may be desirable to lift the MRI scanner above the support stand 610 such that the MRI scanner 660 can be moved from one location to another location or to swap/repair the support stand 610. For example, the MRI scanner 660 may be elevated above the support stand 610 such that one or more vibration isolators can be repaired or replaced. Thus, the example standoffs 682 and housing base channels 618 are configured to mate or be coupled to one or more jacks 650 or a warehouse pallet jack for supporting the cylindrical housing 672 of the MRI scanner 660 such that the MRI scanner 660 can be lifted above the support stand 610.

Figure 7:
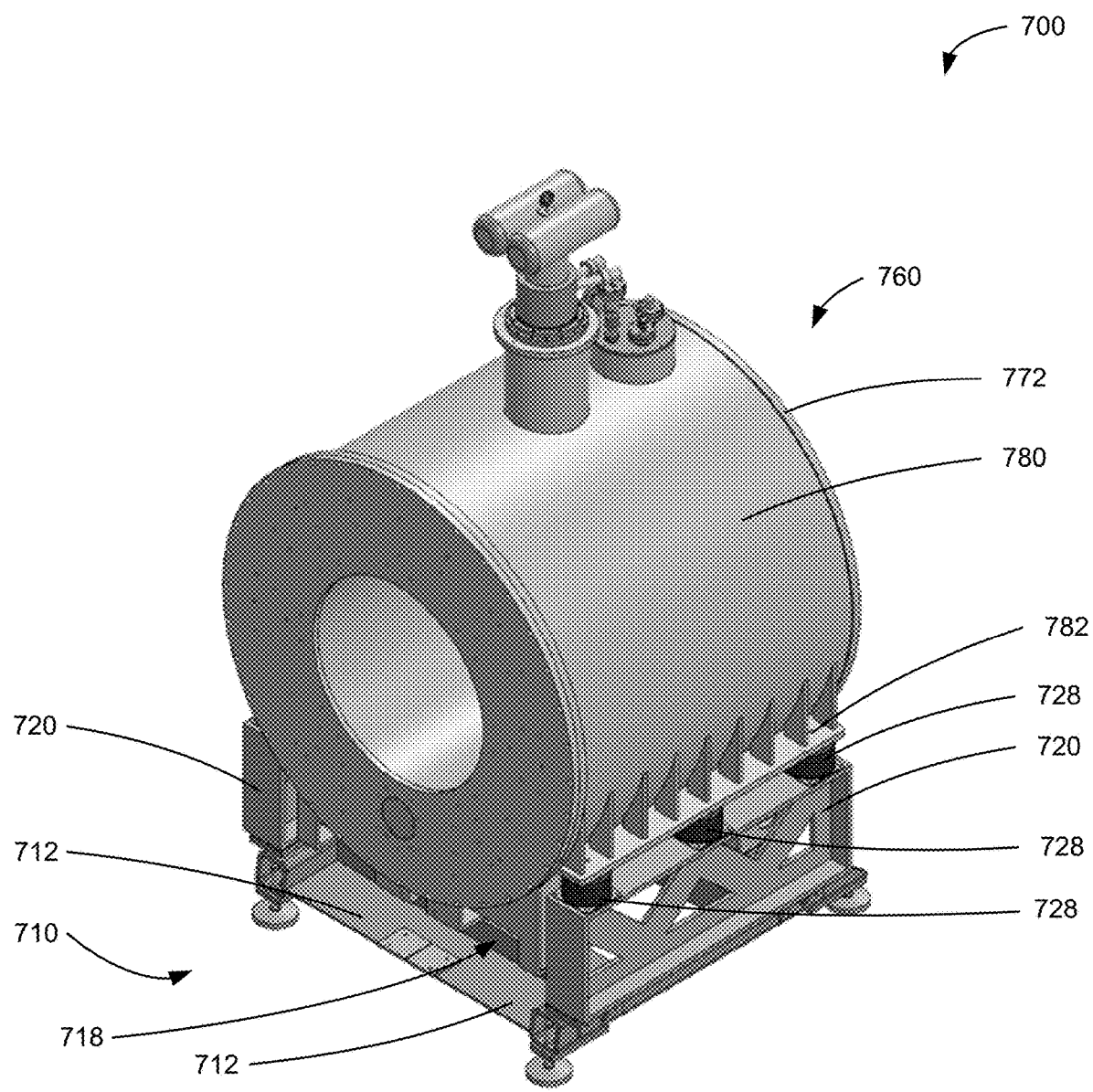
FIG. 7 illustrates a perspective view of a MRI system, in accordance with another example of the present application.

Reference is made to FIG. 7, which illustrates a perspective view of a MRI system 700, in accordance with another example of the present application. The MRI system 700 includes a support stand 710 for supporting a MRI scanner 760.

Similar to the MRI scanners illustrated in FIGS. 5 and 6, the MRI scanner 760 includes a main cylindrical magnet and includes a cylindrical housing 772 for encapsulating the main cylindrical magnet, among other components. Similar to the system of FIG. 6, the cylindrical housing 772 has a lateral surface 780 extending parallel to a horizontal bore from a first bore end to a second bore end. Similar to the system of FIG. 6, the cylindrical housing 772 defines a longitudinal footprint dimension and a lateral footprint dimension. The MRI scanner 760 can include other components, such as computer screens, computer systems, a cryostat, or other components.

The lateral surface 780 can include one or more standoffs 782 protruding or extending from the lateral surface 780. The cylindrical housing 672 can include standoffs 782 on opposing lateral sides of the horizontal bore of the cylindrical housing 772. The standoffs 782 can be similar to the standoffs 682 described in FIG. 6.

The support stand 710 includes a base 712 for positioning the support stand 710 on the floor. In FIG. 7, the support stand 710 includes a pair of pillars 720 extending upright from the base 712. Each of the pair of pillars 720 includes a first end mounted to the base 712 and an opposing second end. The support stand 710 also includes one or more vibration isolators 728 mounted at the second end of respective pillars to support the lateral surface 780 via the standoffs 782.

In FIG. 7, each pillar in the pair of pillars 720 is laterally separated from another pillar of the pair of pillars 720 on an opposing lateral side of the horizontal bore by a lateral separation distance no greater than the lateral footprint dimension. In some examples, each pillar in the pair of pillars 720 extends in a longitudinal direction, such as extending substantially from a first bore end to a second bore end of the horizontal bore. In some examples, the each of the pair of pillars 720 may include a single vibration isolator, such as elastomeric material, that extends in a direction from the first bore end to the second bore end.

In some examples, the MRI systems described herein may include one or more mechanical snubbing devices that can limit motion of MRI scanners supported by support stands described herein. That is, the mechanical snubbing devices can be configured to limit motion of an MRI main magnet or cylindrical housing in the event of a seismic event, such as an earthquake. In some examples, the mechanical snubbing devices can be rigidly mounted to the floor of the MRI examination room.

In some examples, the mechanical snubbing devices may not be coupled to the MRI main magnet or the cylindrical housing during normal operation. The mechanical snubbing devices can be configured such that movement of the main magnet or cylindrical housing exceeding movement that is anticipated during normal MRI scanner operation or a brief seismic event can bring the mechanical snubbing devices into contact with the cylindrical housing. In the present example, when the main magnet or cylindrical housing movement causes the cylindrical housing to contact the mechanical snubbing devices, the mechanical snubbing devices can provide mechanical resistance to further motion exceeding movement that is anticipated during normal MRI scanner operation or a brief seismic event.

In some examples, the above described mechanical snubbing devices can be mounted onto support stands described herein for opposing main magnet or cylindrical housing movement beyond movement that is anticipated during normal MRI scanner operation.

Figure 8:
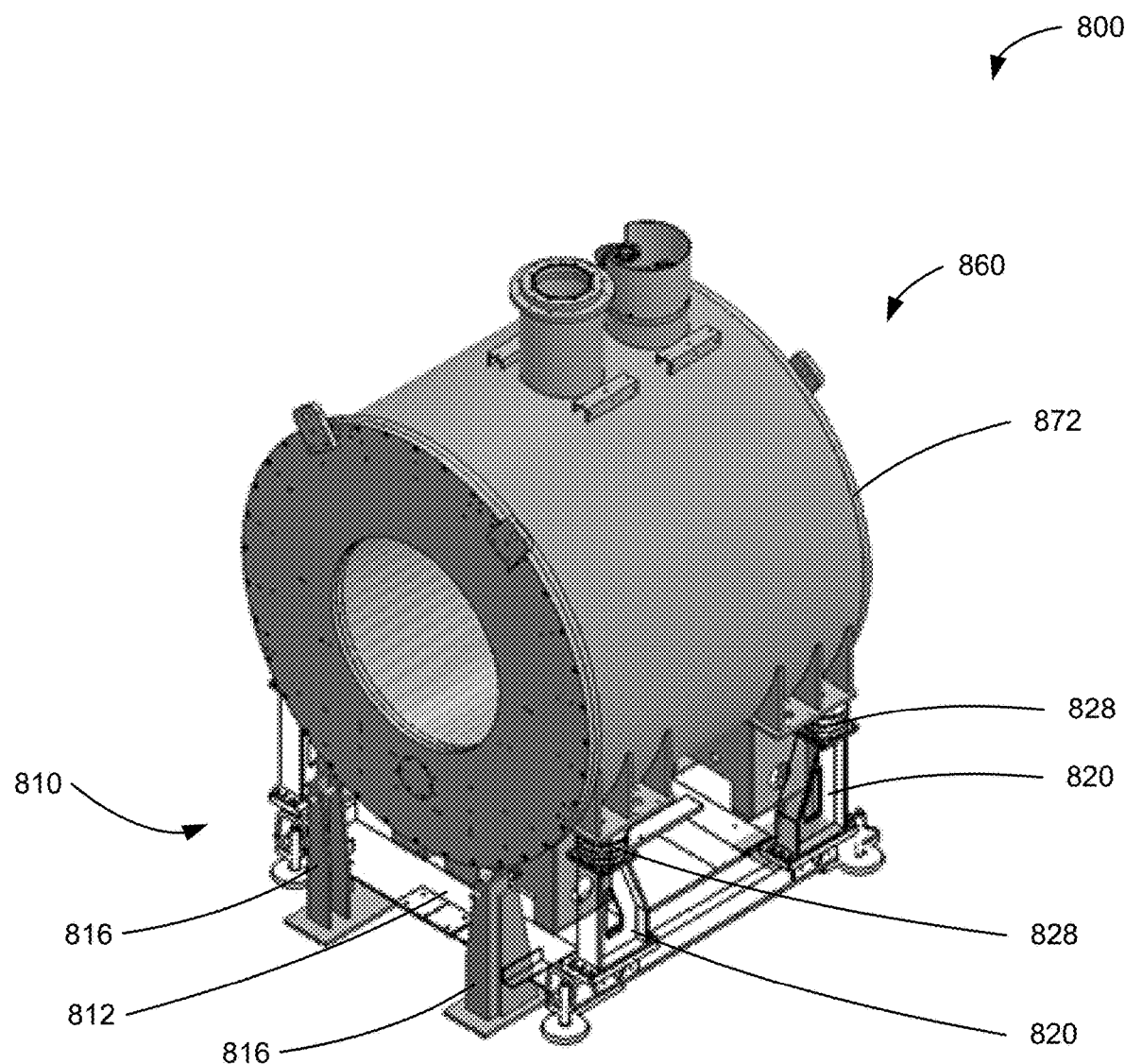
FIG. 8 illustrates a perspective view of a MRI system, in accordance with another example of the present application.

To illustrate, reference is made to FIG. 8, which illustrates a perspective view of a MRI system 800, in accordance with another example of the present application. The MRI system 800 includes a support stand 810 for supporting the MRI scanner 860. Similar to the MRI scanner illustrated in FIG. 7, the MRI scanner 860 includes a main cylindrical magnet and includes a cylindrical housing 872 for encapsulating the main cylindrical magnet, among other components. Similar to the system of FIG. 7, the cylindrical housing 872 defines a longitudinal footprint dimension and a lateral footprint dimension. The MRI scanner 860 can include other components, such as computer screens, computer systems, a cryostat, or other components.

The support stand 810 includes a base 812. In FIG. 8, the support stand 810 includes a plurality of pillars 820 extending upright from the base 812. Each respective pillar 820 has a first end mounted to the base 812 and an opposing second end. The support stand 810 also includes a vibration isolator 828 mounted at the second end of respective pillars to support a lateral surface of the cylindrical housing 872.

The MRI system 800 also includes one or more mechanical snubbing devices 816. The mechanical snubbing devices 816 can be affixed to or adjacent to the support stand 810. The one or more mechanical snubbing devices 816 may not be directly attached to the cylindrical housing 872, but may be configured to provide mechanical resistance to movement of the cylindrical housing 872 that is beyond movement or vibration expected during normal MRI scanner 860 operation or that is beyond movement expected during common seismic events in the region that the MRI scanner 860 is located.

When the mechanical snubbing devices 816 are positioned adjacent to the support stand 810, the mechanical snubbing devices 816 can be secured to the floor of the examination room within which the MRI scanner 860 is located. In some examples, one or more of the mechanical snubbing devices 816 may be secured to the floor of the examination room and configured to resist movement of the support stand 810 that is greater than vibration or movement expected during normal MRI scanner 860 operation. Variations of positioning of the mechanical snubbing devices 816 relative to the support stand 810 and to the cylindrical housing 872 illustrated in FIG. 8 can be contemplated.

Although the support stand examples described herein relate to MRI scanners, it is understood that features of the support stand may be adapted for other medical diagnostic systems that may be susceptible to vibrations or that may generate appreciable vibrations.

Certain adaptations and modifications of the described embodiments can be made. Therefore, the above discussed embodiments are considered to be illustrative and not restrictive.

What is claimed is:

1. A support stand for supporting a magnetic resonance imaging (MRI) scanner while in operation, the MRI scanner including a cylindrical housing having a lateral surface extending parallel to a horizontal bore from a first bore end to a second bore end to encapsulate a main cylindrical magnet, the cylindrical housing defining a longitudinal footprint dimension and a lateral footprint dimension, the support stand comprising:
a base for positioning the support stand on a floor;
a plurality of pillars extending upright from the base, each respective pillar having a first end mounted to the base and an opposing second end in an isolation plane that is parallel to the base, the isolation plane intersecting a center of gravity of the MRI scanner; and
a vibration isolator mounted at the second end of respective pillars to support the lateral surface of the cylindrical housing,
wherein a respective pillar in a pair of pillars is laterally separated from another pillar of that pair on an opposing lateral side of the horizontal bore by a lateral separation distance no greater than the lateral footprint dimension,
and wherein a respective pillar in the plurality of pillars is longitudinally separated from another pillar in the plurality of pillars by a longitudinal separation distance no greater than the longitudinal footprint dimension.

2. The support stand of claim 1, wherein the lateral footprint dimension is a diameter of the cylindrical housing.

3. The support stand of claim 1, wherein the longitudinal footprint dimension is a length of the cylindrical housing.

4. The support stand of claim 1, wherein the vibration isolator includes elastomeric material for minimizing transmission of environment borne vibration to the MRI scanner and for minimizing transmission of MRI scanner generated vibration to the environment.

5. The support stand of claim 1, wherein the vibration isolator includes at least one of a hollow elastomeric capsule, a metallic cylinder, or a closed vessel including a combination of elastomeric and metal materials for encapsulating air.

6. The support stand of claim 1, wherein the vibration isolator includes an air bladder adjustably inflatable with a pneumatic air supply source.

7. The support stand of claim 1, wherein each respective pillar includes a beveled surface at the second end to angle the respective vibration isolator towards the lateral surface to support the cylindrical housing.

8. The support stand of claim 1, wherein the support stand is fixed to the lateral surface of the cylindrical housing.

9. The support stand of claim 1, further comprising a tuned mass damper coupled to at least one of the base or one or more pillars for reducing harmonic vibration.

10. The support stand of claim 1, further comprising one or more base channels in a bottom base surface of the base to receive a fork of a pallet jack configurable to raise the support stand and to transport the MRI scanner.

11. The support stand of claim 1, further comprising an attachment hook positioned on the base proximal to at least one of the first bore end or the second bore end to receive a patient table.

12. The support stand of claim 1, wherein the base or the plurality of pillars are constructed of substantially non-ferrous material including at least one of aluminum, SAE 316 stainless steel, fiberglass, plastic, brass, or epoxy.

13. The support stand of claim 1, wherein the plurality of pillars includes at least four pillars, and wherein each respective pillar is mounted substantially proximal to an edge of the base to collectively define an equiangular quadrilateral perimeter.

14. A magnetic resonance imaging (MRI) system comprising:
a MRI scanner including:
a main cylindrical magnet having a horizontal bore extending parallel to a floor and extending from a first bore end to a second bore end; and
a cylindrical housing encapsulating the main cylindrical magnet, the cylindrical housing having a lateral surface extending parallel to the horizontal bore from the first bore end to the second bore end, the cylindrical housing including a plurality of standoffs extending from the lateral surface of the cylindrical housing, each respective standoff being mounted to a respective vibration isolator, wherein the cylindrical housing defines a longitudinal footprint dimension and a lateral footprint dimension; and
a support stand for supporting the MRI scanner while in operation, the support stand including:
a base for positioning the support stand on the floor;
a plurality of pillars extending upright from the base, each respective pillar having a first end mounted to the base and an opposing second end; and
a vibration isolator mounted at the second end of respective pillars to support the lateral surface of the cylindrical housing,
wherein a respective pillar in a pair of pillars is laterally separated from another pillar of that pair on an opposing lateral side of the horizontal bore by a lateral separation distance no greater than the lateral footprint dimension,
and wherein a respective pillar in the plurality of pillars is longitudinally separated from another pillar in the plurality of pillars by a longitudinal separation distance no greater than the lateral footprint dimension.

15. The MRI system of claim 14, wherein the second end of each respective pillar is in an isolation plane that is parallel to the base.

16. The MRI system of claim 15, wherein the isolation plane intersects a center of gravity of the MRI scanner.

17. The MRI system of claim 14, further comprising one or more base channels in a bottom base surface of the base to receive a fork of a pallet jack configurable to raise the support stand and to transport the MRI scanner.

18. The MRI system of claim 14, wherein the lateral footprint dimension is a diameter of the cylindrical housing.

19. The MRI system of claim 14, wherein the longitudinal footprint dimension is a length of the cylindrical housing.

20. The MRI system of claim 14, wherein the vibration isolator includes elastomeric material for minimizing transmission of environment borne vibration to the MRI scanner and for minimizing transmission of MRI scanner generated vibration to the environment.

* * * * *